United States Patent [19]

Ellrich et al.

[11] Patent Number: 4,792,632

[45] Date of Patent: Dec. 20, 1988

[54] BISACYLPHOSPHINE OXIDES, THE PREPARATION AND USE THEREOF

[75] Inventors: Klaus Ellrich, Munich; Christian Herzig, Seefeld, both of Fed. Rep. of Germany

[73] Assignee: ESPE Fabrik Pharmazeutischer Praparate GmbH, Oberbayern, Fed. Rep. of Germany

[21] Appl. No.: 121,803

[22] Filed: Nov. 17, 1987

Related U.S. Application Data

[62] Division of Ser. No. 801,339, Nov. 25, 1985, Pat. No. 4,737,593.

[30] Foreign Application Priority Data

Nov. 27, 1984 [DE] Fed. Rep. of Germany ..... 34432213

[51] Int. Cl.$^4$ ............................................. C07F 9/53
[52] U.S. Cl. ....................... 568/15; 204/157.6; 204/157.81; 204/157.87; 430/910; 430/921
[58] Field of Search ...................... 568/15; 204/157.6; 430/910, 921

[56] References Cited

U.S. PATENT DOCUMENTS

| | | | |
|---|---|---|---|
| 4,298,738 | 11/1981 | Lechtken et al. ............... | 546/22 |
| 4,324,744 | 4/1982 | Lechtken et al. ............... | 568/15 X |
| 4,522,693 | 6/1985 | Henne et al. ................... | 568/15 X |
| 4,737,593 | 4/1988 | Ellrich et al. .................. | 568/15 |

OTHER PUBLICATIONS

Chemical Abstracts, vol. 78, 123782z (1973).
Chemical Abstracts, vol. 89, 163679e (1978).
Chemical Abstracts, vol. 90, 87589d (1979).
Chemical Abstracts, vol. 99, 5695j (1983).
Chemical Abstracts, vol. 99, 175893q (1983).

*Primary Examiner*—Werren B. Lone

*Attorney, Agent, or Firm*—Birch, Stewart, Kolasch & Birch

[57] ABSTRACT

Bisacylphosphine oxides of the general formula

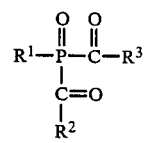

wherein
$R^1$ stands, for example, for a straight-chain or branched $C_{1-18}$ alkyl radical,
a cyclohexyl, cyclopentyl, phenyl, naphthyl, or biphenylyl radical,
a cyclopentyl, cyclohexyl, phenyl, naphthyl, or biphenylyl radical substituted by F, Cl, Br, I, $C_1$-$C_{12}$ alkyl and/or $C_1$-$C_{12}$ alkoxyl, or
an S or N-containing 5-membered or 6-membered heterocyclic ring, and
$R^2$ and $R^3$, which are the same or different, stand for a cyclohexyl, cyclopentyl, phenyl, naphthyl, or biphenylyl radical,
a cyclopentyl, cyclohexyl, phenyl, naphthyl, or biphenylyl radical substituted by F, Cl, Br, I, $C_{1-4}$ alkyl and/or $C_{1-4}$ alkoxyl, or
an S or N-containing 5-membered or 6-membered heterocyclic ring; or
$R^2$ and $R^3$ are joined to form a ring which contains from 4 to 10 carbon atoms and which may be substituted by 1 to 6 $C_{1-4}$ alkyl radicals.

The compounds are prepared by oxidation of the corresponding bisacylphosphines. The compounds are suitable for use as initiators for the photopolymerization of compounds containing ethylenically unsaturated bonds.

10 Claims, No Drawings

BISACYLPHOSPHINE OXIDES, THE PREPARATION AND USE THEREOF

This application is a divisional of copending application Ser. No. 801,339, filed on Nov. 25, 1985, now U.S. Pat. No. 4,737,593.

BACKGROUND AND FIELD OF THE INVENTION

The present invention relates to novel bisacylphosphine oxides, the preparation thereof, and their use as photoinitiators in photopolymerizable compositions.

A number of photoinitiators based on acylphosphines are known. U.S. Pat. No. 3,668,093 and German Offenlegungsschrift No. 3,020,092, for example, describe acylphosphines as photoinitiators. European publications Nos. 0 073 413, 0 007 508, 0 057 474 describe monoacylphosphine oxides as photoinitiators. However, photopolymerizable compositions cured with the initiator systems of U.S. Pat. No. 3,668,093 exhibit unsatisfactory color stability and photopolymerizable compositions cured with the initiator systems of U.S. Pat. No. 3,668,093, German Offenlegungsschrift No. 3,020,092, and the European publications Nos. 0 073 413, 0 007 508 and 0 057 474 cure only to a shallow depth, have low curing rates and exhibit unsatisfactory storage stability. Furthermore, it is a disadvantage that the initiators of the above publications only have a low absorption in the range of visible light, i.e., wavelength >400 nm, so that only low light yields can be attained in this range. However, the use of this "harmless" light is particularly indispensable for many applications, e.g. in the dental field.

DESCRIPTION OF THE INVENTION

Therefore, it is an object of the invention to provide novel acylphosphine oxides which overcome the disadvantages of the above discussed previous initiators.

The subject matter of the invention relates to bisacylphosphine oxides of the general formula

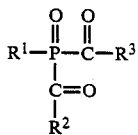

wherein
$R^1$ stands for a straight-chain or branched $C_{1-18}$ alkyl radical, a cyclohexyl, cyclopentyl, phenyl, naphthyl, or biphenylyl radical,
a cyclopentyl, cyclohexyl, phenyl, naphthyl, or biphenylyl radical substituted by F, Cl, Br, I, $C_1$-$C_{12}$ alkyl and/or $C_1$-$C_{12}$ alkoxyl,
an S or N-containing 5-membered or 6-membered heterocyclic ring, or
a radical of the general formula

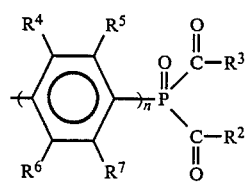

wherein
n is 1 or 2, and
$R^4$, $R^5$, $R^6$ and $R^7$ are H, $C_{1-4}$ alkyl, $C_{1-4}$ alkoxyl, F, Cl or Br;
$R^2$ and $R^3$, which are the same or different, stand for a cyclohexyl, cyclopentyl, phenyl, naphthyl, or biphenylyl radical, a cyclopentyl, cyclohexyl, phenyl, naphthyl, or biphenylyl radical substituted by F, Cl Br, I, $C_{1-4}$ alkyl and/or $C_{1-4}$ alkoxyl, or an S or N-containing 5-membered or 6-membered heterocyclic ring; or
$R^2$ and $R^3$ are joined to form a ring containing from 4 to 10 carbon atoms and being optionally substituted by 1 to 6 $C_{1-4}$ alkyl radicals.

The bisacylphosphine oxides of the invention exhibit very good reactivity as photoinitiators for photopolymerizable monomers having at least one ethylenically unsaturated bond, and mixtures thereof with one another and with known additives. The bisacylphosphine oxides of the invention are suited especially well as photoinitiators for photopolymerizable dental compositions such as tooth filling compositions, material for crowns and bridges, seal and bond solutions. Moreover, the photoinitiators of the invention are suited for the preparation of photopolymerizable compositions suited for use as moldings, and also, for example, for sheets, films or coatings.

The photopolymerizable compositions prepared with the bisacylphosphine oxides of the invention are far superior to photopolymerizable compositions prepared with hitherto known photoinitiators regarding color stability, storage stability, attainable curing depths and curing rates. A further advantage resides in the low oxygen inhibition during photopolymerization with the bisacylphosphine oxides of the invention.

In the compounds of the invention, $R^1$ preferably stands for decyl, phenyl, naphthyl, 4-biphenylyl 2-methylphenyl, 1-methylnaphthyl, 2,5-dimethylphenyl, 4-propylphenyl, 4-octophenyl, 4-chlorophenyl or 4-ethoxy phenyl.

$R^2$ and $R^3$ preferably stand for phenyl radicals substituted in the 2- and 6-positions, or naphthyl radicals substituted in the 2-position. $R^2$ and $R^3$ especially stand for phenyl, naphthyl, 2,6-dichlorophenyl, 2,6-dimethoxyphenyl, 2-methyl-naphthyl, 2-methoxynaphthyl, 2,6-dimethylphenyl, or 2,4,6-trimethylphenyl.

Specific examples for $R^1 = C_{1-18}$ alkyl are methyl, propyl, iso-butyl, t-butyl, iso-pentyl, octyl, and decyl.

Specific examples for the $C_1$-$C_2$ alkyl radicals in $R^1$=alkyl or alkoxy-substituted cyclopentyl, cyclohexyl, phenyl, naphthyl or biphenylyl radical are methyl, ethyl, n-propyl, iso-, t-, or n-butyl, pentyl, octyl, and decyl.

Examples for the $C_{1-4}$ alkyl radicals, utilized in defining $R^2$-$R^7$, are methyl, ethyl, propyl, iso-propyl, iso-butyl, t-butyl, and n-butyl.

The following compounds are specific preferred examples for the bisacylphosphine oxides of the invention:
bis-(2,6-dichlorobenzoyl)phenylphosphine oxide
bis-(2,6-dichlorobenzoyl)-2,5-dimethylphenylphosphine oxide
bis-(2,6-dichlorobenzoyl)-4-ethoxyphenylphosphine oxide
bis-(2,6-dichlorobenzoyl)-4-biphenylylphosphine oxide
bis-(2,6-dichlorobenzoyl)-4-propylphenylphosphine oxide
bis-(2,6-dichlorobenzoyl)-2-naphthylphosphine oxide
bis-(2,6-dichlorobenzoyl)-1-napthylphosphine oxide bis-(2,6-dichlorobenzoyl)-4-chlorophenylphosphine oxide
bis-(2,6-dichlorobenzoyl)-2,4-dimethoxyphenylphosphine oxide
bis-(2,6-dichlorobenzoyl)decylphosphine oxide
bis-(2,6-dichlorobenzoyl)-4-octylphenylphosphine oxide
bis-(2,6-dimethoxybenzoyl)-2,5-dimethylphenylphosphine oxide
bis-(2,6-dimethoxybenzoyl)phenylphosphine oxide
bis-(2,4,6-trimethylbenzoyl)-2,5-dimethylphenylphosphine oxide
bis-(2,6-dichloro-3,4,5-trimethoxybenzoyl)-2,5-dimethylphenylphosphine oxide
bis-(2,6-dichloro-3,4,5-trimethoxybenzoyl)-4-ethoxyphenylphosphine oxide
bis-(2-methyl-1-naphthoyl)-2,5-dimethylphenylphosphine oxide
bis-(2-methyl-1-naphthoyl)phenylphosphine oxide
bis-(2-methyl-1-naphthoyl)-4-biphenylylphosphine oxide
bis-(2-methyl-1-naphthoyl)-4-ethoxyphenylphosphine oxide
bis-(2-methyl-1-naphthoyl)-2-naphthylphosphine oxide
bis-(2-methyl-1-naphthoyl)-4-propylphenylphosphine oxide
bis-(2-methyl-1-naphthoyl)-2,5-dimethylphosphine oxide
bis-(2-methoxy-1-naphthoyl)-4-ethoxyphenylphosphine oxide
bis-(2-methoxy-1-naphthoyl)-4-biphenylylphosphine oxide
bis-(2-methoxy-1-naphthoyl)-2-naphthylphosphine oxide
bis-(2-chloro-1-naphthoyl)-2,5-dimethylphenylphosphine oxide The bisacylphosphine oxides are prepared, according to the invention, by oxidation of the partially already known bisacylphosphines. $O_2$, $NO_2$, $H_2O_2$ and other oxidizing agents familiar to those skilled in the art may be employed.

The desired bisacylphosphines are obtained, for example, by reaction of the mono-substituted phosphines of the formula $R^1PH_2$ with stoichiometric quantities of acyl chlorides $R^2COCl$, $R^3COCl$, wherein $R^1$, $R^2$ and $R^3$ are as defined above. HCl is eliminated in a manner known per se, preferably with the use of an auxiliary base, such as tertiary amine.

Suitable photopolymerizable monomers for use with the bisacylphosphines of the invention are compounds and substances with polymerizable CC double bonds familiar to those skilled in the art which are suitably activated by aryl, carbonyl, ester, carboxy, or cyanide groups, for example. For example, acrylic acid and methacrylic acid and their esters with monohydric or polyhydric alcohols having up to 20 carbon atoms, such as methyl methacrylate, ethyl methacrylate, and triethylene glycol dimethacrylate can be polymerized by use of the bisacylphosphines. Furthermore, acrylic and methacrylic derivatives of bisphenol A, e.g. the monomers mentioned in German Pat. No. 1,921,869 and U.S. Pat. No. 3,066,112 (which are hereby incorporated by reference), can be employed.

Further useful compounds polymerizable according to the invention are alkanediol diacrylates and alkanediol dimethacrylates, such as 1,6-hexanediol di(meth)acrylate, 1,4-butanediol di(meth)acrylate, tri- or tetraethylene glycol di(meth)acrylate, and the diacrylates and dimethacrylates of bis-hydroxymethyl tricyclo [5.2.1.0.$^{2,6}$]-decane mentioned in German Pat. No. 2,816,823, which is hereby incorporated by reference. Also the reaction products of diisocyanates and hydroxyalkyl(meth)acrylates can be used, as described, for example, in German Offenlegungsschrift No. 2,312,559 (hereby incorporated by reference), adducts of diisocyanates and 2,2-propane-bis-3-(4-phenoxy)-1,2-hydroxypropane-1-methacrylate according to U.S. Pat. No. 3,629,187 (hereby incorporated by reference) and the adducts of isocyanates and methacroyl alkyl ethers, adducts of isocyanates and methacroyl alkoxybenzoles and adducts of isocyanates and methacroyl akoxycycloalkanes, as described in the European publication 44,352 (hereby incorporated by reference).

Of course, mixtures of suitable monomers can also be employed. Furthermore, aromatic vinyl compounds, such as styrene and derivatives thereof, e.g., α-alkyl derivatives of styrene, like α-methyl styrene and vinyl toluene, can be polymerized by the bisacylphosphines oxides of the invention.

Higher molecular weight compounds polymerizable according to the invention, are, for example, unsaturated polyesters prepared by the reaction of α,β—unsaturated dicarboxylic acids—optionally in mixture with saturated dicarboxylic acids—with alkanediols.

To the photopolymerizable compounds whose composition for a particular purpose is familiar to those skilled in the art there can be added, in a manner known per se, saturated and/or unsaturated polymers and further additives, such as thermal polymerization inhibitors, pigments, dyes, peroxides and fillers. Such mixtures are per se known to those skilled in the art, and the type and quantity of the additives depend on the contemplated purpose.

The bisacylphosphine oxides of the invention are generally employed at a concentration of about 0.01 to about 15% by weight, preferably 0.05 to 5% by weight, based on the photopolymerizable composition. They optionally can be combined with accelerators and/or other photoinitiators. Accelerators per se known to those skilled in the art are, for example, secondary and/or tertiary amines, phosphites, sulfinic and barbituric acid derivatives. Furthermore, the bisacylphosphine oxides, optionally in the presence of the above indicated accelerators, can be used in combination with other photoinitiators for photo-curing photopolymerizable compositions. Such other photoinitiators are, for example, aromatic ketones such as benzil ketals, benzoine ethers, benzoine esters, thioxanthones and 1,2-diketones, e.g. camphor quinone.

As radiation sources for the light initiating the polymerization of such mixtures, sources are generally used which emit the light preferably in the absorption range of the compounds of the invention, e.g. between 200 and 500 nm. For curing dental compositions light of a wavelength between 400 and 500 nm is especially suited. Especially preferred are optionally doped mercury low-pressure, medium-pressure, and high-pressure radiators, superactinic fluorescent tubes, pulse radiators and incandescent lamps, e.g. halogen lamps.

A special advantage of the bisacylphosphine oxides of the invention is the characteristic that they are suitable as photoinitiators by which photopolymerization is possible with longer-wave, and thus less hazardous, light sources, such as fluorescent tubes, or with sunlight.

PREPARATION OF COMPOUND ACCORDING TO INVENTION

EXAMPLE 1

(a) Bis-(2,6-dichlorobenzoyl)-2,5-dimethylphenylphosphine 13.8 grams of 2,5-dimethylphenylphosphine are added to 46.6 grams of 2,6-dichlorobenzoyl chloride in 60 ml toluene at 20° C. The mixture is heated to 90° C., whereupon 22.2 grams of dry triethylamine are added within a period of 5 minutes. To complete the reaction, the composition is stirred for 5 hours at the same temperature. After dilution of the reaction composition the product is scrubbed 2 times with water and diluted bicarbonate solution, the organic phase is dried and concentrated under vacuum. The captioned compound is obtained in the form of a yellow crystalline composition of >95% purity (HPLC). Yield: 50 grams.

(b) Bis-(2,6-dichlorobenzoyl)-2,5-dimethylphenylphosphine Oxide

The crude bis-(2,6-dichlorobenzoyl)-2,5-dimethylphenylphosphine (50 grams) is dissolved in 1 liter acetonitrile, mixed with 150 ml of 30% hydrogen peroxide, and heated for one hour at 60° C. The formation of the phosphine oxide is accompanied by deepening of the color, and it precipitates in crystalline form, after the addition of water and cooling. Recrystallization from acetonitrile/water yields 37 grams of the captioned compound (74% of theroretical yield in 2 steps)

| | |
|---|---|
| m.p. | 172° C. |
| UV | $\lambda$max = 366 nm ($\epsilon_{mol}$ = 1065) |
| $^{31}P-NMR$ | $\delta$ = +9.1 ppm (against $H_3PO_4$ ext.) |
| $^{1}H-NMR$ | $\delta$ = 2.30 ppm (s; 3H) |
| | 2.65 ppm (d, J(PCCCH) = 1 Hz; 3H) |
| | 7.05–7.35 ppm (m; 8H) |
| | 7.26 ppm (d, J(PCCH) = 13 Hz; 1H) |
| IR | $\gamma$ (C = O) = 1703 cm$^{-1}$ |
| | $\gamma$ (P = O) = 1200 cm$^{-1}$ |
| Elemental analysis: | $C_{22}H_{15}Cl_4O_3P$ (500.14) |
| calculated | C 52.83%  H 3.02%  Cl 28.36% |
| found | C 52.72%  H 3.07%  Cl 28.04% |

The compounds contained in Table 1 are obtained following procedures analogous to Example 1.

TABLE 1

| Compound | Melting Point (°C.) | $^{31}P-NMR$ (ppm) | UV $\lambda$max. ($\epsilon_{mol}$) | $\epsilon_{mol}$ at 400 nm |
|---|---|---|---|---|
| Bis-(2,6-dichlorobenzoyl)-phenylphosphine oxide | 193–194 | 2.9 | 363 nm (1130) | 607 |
| Bis-(2,6-dichlorobenzoyl-2,5-dimethylphenylphosphine oxide | 161–164 | 9.1 | 360 nm (1065) | 580 |
| Bis-(2,6-dichlorobenzoyl)-4-ethoxyphenylphosphine oxide | 173–174 | 4.2 | 364 nm (1640) | 690 |
| Bis-(2,6-dichlorobenzoyl)-4-octylphenylphosphine oxide | 141–142 | 4.1 | 390 nm (670) | 620 |
| Bis-(2,6-dichlorobenzoyl)-decylphosphine oxide | 95–96 | 25.9 | 407 nm (480) | 470 |
| Bis-(2,6-dichlorobenzoyl)-4-biphenylylphosphine oxide | 209–210 | 3.2 | 364 nm (2060) | 800 |
| Bis-(2,6-dimethoxybenzoyl)-2,5-dimethylphenylphosphine oxide | 50+ | 17.6 | — | 505 |
| Bis-(2,6-dimethoxybenzoyl)-phenylphosphine oxide | 174–176 | 8.6 | — | 550 |
| Bis-(2,6-dichloro-3,4,5-trimethoxybenzoyl)-2,5-dimethylphenylphosphine oxide | 123–124 | 8.7 | — | 640 |
| Bis-(2-methyl-1-naphthoyl)-phenylphosphine oxide | | 8.8 | 323 nm (4900) | 1040 |
| Bis-(2-methyl-1-naphthoyl)-4-biphenylylphosphine oxide | 189–193 | 9.1 | 350 nm (5600) | 1680 |
| Bis-(2-methoxy-1-naphthoyl-2,5-dimethylphenylphosphine oxide | 197–199 | 21.0 | — | 2550 |
| Bis-(2-methoxy-1-naphthoyl-4-ethoxyphenylphosphine oxide | 191–192 | 12.2 | — | 2700 |

+Softening Point

USE OF THE COMPOUNDS OF THE INVENTION

EXAMPLE 2

70 parts by weight of bis-acryloxymethyl-tricyclo-[5.2.1.0.$^{2,6}$]-decane and 30 parts by weight of 2,2-bis-4-(3-methacryloxy-2-hydroxypropoxy)-phenylpropane (Bis-GMA) are stirred while carefully heated until a clear solution I is formed.

The solution I is cooled to room temperature and 0.5% by weight of a photoinitiator (selected from those listed in Table 2) are added with stirring until the solution is clear.

The resulting solution is introduced into a cylinder (5 mm diameter, 8 mm length; for greater thicknesses 20 mm). Thereafter the solution is exposed to radiation from a commercial dental radiator (Elipar-Visio/Espe) for 20 seconds, the polymer is removed from the cylinder, the soft or gel-like, incompletely polymerized components are removed with a plastic spatula, and the attained thickness of the layer is measured. To this end the solutions are stored prior to polymerization for 1 day and 1 month, respectively, in the absence of light. The results are listed in Table 2.

TABLE 2

| Photoinitiator | Layer Thickness (mm) after 24 hrs | Layer Thickness (mm) after 1 month | Thickness Loss % | Extinction at 400 nm |
|---|---|---|---|---|
| 2,6-Dichlorobenzoyl-diphenylphosphine oxide (European publication No. 7508) | 7 | 6.5 | 7 | 190 |
| 2,6-Dichlorobenzoyl-bis-(2,5-dimethylphenyl)phosphine oxide | 5.1 | 4.1 | 20 | 440 |
| Bis-(2,6-dichlorobenzoyl)-phenyl-phosphine oxide (invention) | 15 | 14.5 | 3 | 607 |
| Bis-(2,6-dichlorobenzoyl)-2,5-dimethylphenylphosphine oxide (invention) | 15 | 14.5 | 3 | 580 |

The bisacylphosphine oxides of the invention exhibit surprisingly increased extinction in the wavelength range >400 nm, compared with the monoacylphosphine oxides of the prior art, they attain more than twice the sheet thickness, and their performance drop after one month is only 3% (as compared with 7 to 20% for the monoacylphosphine oxides).

EXAMPLE 3

Preparation of a photopolymerizable tooth filling composite:
15 parts by weight of bis-acryloxymethyl-tricylco-[5.2.1.0.$^{2,6}$]-decane
15 parts by weight of bis-GMA, and
7 parts by weight of silanized pyrogenic silicic acid as a premix is kneaded.

1.84 gram of said premix and 1.66 gram of solution I from Example 2 are prekneaded for 5 minutes. Thereafter a total of 15 grams of silanized quartz pigmented to resemble the color of teeth (average particle size about 6 microns) are added and kneaded to obtain a tooth filling composite of uniform pasty consistency. When the paste is filled into the mold described in Example 2, a completely polymerized sheet thickness of 5 mm is obtained after 20 seconds of exposure to light from a commercial dental radiator (Elipar-Visio lamp/Espe). The resistance of the polymer to pressure is 300 MPa.

EXAMPLE 4

Tooth filling composites prepared according to Example 3 with the use of the photoinitiators listed in Table 3 are filled into cylinders (3 mm diameter, 3 mm height) in the middle of which the temperature can be measured during the polymerization. After 20 seconds of exposure to light from a commercial dental radiator (Elipar-Visio lamp/Espe) the structures are taken out and the soft layer is removed with toluene. From the weight difference the amount of uncured material in mg/cm$^2$ at the upper and lower surface of the cylinder is calculated. Moreover, the temperature course in time is followed by the thermosensor and a measuring instrument connected thereto. The results are listed in the following Table 3.

TABLE 3

| Photoinitiator | Tmax (°C.) | Time for reaching Tmax (sec) | Soft Layer (mg/cm$^2$) |
|---|---|---|---|
| 2,4,6-Trimethyl-benzoyldiphenyl-phosphine oxide (European publication No. 7508) | 39.8 | 18 | 1.8/2.0 |
| Bis-(2,6-dichloro-benzoyl)-2,5-dimethylphenylphosphine oxide (invention) | 43.7 | 16 | 1.0/1.1 |

It is evident that the bisacylphosphine oxide of the invention exhibits a higher polymerization rate and lower oxygen inhibition than the prior art initiator.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method of polymerizing a photopolymerizable composition comprising adding a bisacylphosphine oxide having the formula

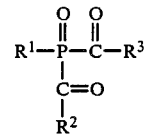

wherein
R$^1$ stands for a straight-chain or branched C$_{1-18}$ alkyl radical, a cyclohexyl, cyclopentyl, phenyl, naphthyl, or biphenyl radical,
a cyclopentyl, cyclohexyl, phenyl, naphthyl or biphenylyl radical substituted by F, Cl, Br, I, C$_1$–C$_{12}$ alkyl and/or C$_1$–C$_{12}$ alkoxyl,
an S or N-containing 5-membered or 6-membered heterocyclic ring, or
a radical of the formula:

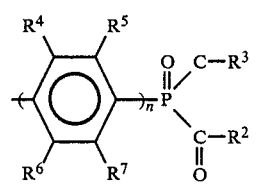

wherein
n is 1 or 2, and
R$^4$, R$^5$, R$^6$ and R$^7$ are H, C$_{1-4}$ alkyl, C$_{1-4}$ alkoxyl, F, Cl or Br;

$R^2$ and $R^3$, which are the same or different, stand for a cyclohexyl, cyclopentyl, phenyl, naphthyl, or biphenylyl radical a cyclopentyl, cyclohexyl, phenyl, naphthyl or biphenylyl radical substituted by F, Cl, Br, I, $C_{1-4}$ alkyl and/or $C_{1-4}$ alkoxyl, or an S or N-containing 5-membered or 6-membered heterocyclic ring; or $R^2$ and $R^3$ are joined to form a ring containing 4 to 10 carbon atoms and being optionally substituted by 1 to 6 $C_{1-4}$ alkyl radicals as a photoinitiator to a photopolymerizable composition and exposing the thus obtained mixture to light.

2. A method according to claim 1, wherein said photopolymerizable composition comprises monomers having ethylenically unsaturated bonds.

3. A method according to claim 1, wherein said photopolymerizable composition comprises acrylic acid or methacrylic acid or esters thereof with $C_{1-20}$ monohydric alcohols or polyhydric alcohols; acrylic or methacrylic derivatives of bisphenol A; alkanediol diacrylates or alkanediol dimethacrylates, diacrylates or dimethacrylates of bis-hydroxymethyl tricyclo[5.2.1.0.$^{2,6}$]-decane; reaction products of diisocyanates and hydroxyalkyl(meth)acrylates; adducts of diisocyanates and 2,2-propane-bis-3-(4-phenoxy)-1,2-hydroxypropane-1-methacrylate; adducts of isocyanates and methacroyl alkyl ethers; adducts of isocyanates and methacroyl alkoxybenzoles; adducts of isocyanates and methacroyl alkoxycycloalkanes; aromatic vinyl compounds; styrene or derivatives thereof; α-alkyl derivatives of styrene; unsaturated polyesters prepared by the reaction of α,β-unsaturated dicarboxylic acids with alkanediols; or unsaturated polyesters prepared by the reaction of alkanediols with α,β-unsaturated dicarboxylic acids in mixture with saturated dicarboxylic acids.

4. A method according to claim 3, wherein said photopolymerizable composition comprises methyl methacrylate, ethyl methacrylate, triethylene glycol dimethacrylate, 1,6-hexanediol di(meth)acrylate, 1,4-butandiol di(meth)acrylate, triethylene glycol di(meth)acrylate, tetraethylene glycol di(meth)acrylate, bis-acryloxymethyl-tricyclo-[5.2.1.0.$^{2,6}$]-decane, 2,2-bis-4-(3-methacryloxy-2-hydroxypropoxy)-phenylpropane, styrene, α-methylstyrene or vinyl toluene.

5. A method according to claim 3, wherein said bisacylphosphine oxide is added in an amount of about 0.01 to about 15% by weight based on the photopolymerizable composition.

6. A method according to claim 1, wherein said light is in the range of between about 200 to 500 nm.

7. A polymerization product prepared by the process according to claim 4.

8. A polymerization product according to claim 7 which is a dental composition.

9. A photopolymerizable composition comprising a bisacylphosphine oxide having the formula

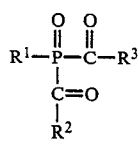

I wherein $R^1$ stands for a straight-chain or branched $C_{1-18}$ alkyl radical, a cyclohexyl, cyclopentyl, phenyl, naphthyl, or biphenyl radical, a cyclopentyl, cyclohexyl, phenyl, naphthyl or biphenylyl radical substituted by F, Cl, Br, I, $C_1$-$C_{12}$ alkyl and/or $C_1$-$C_{12}$ alkoxyl, an S or N-containing 5-membered or 6-membered heterocyclic ring, or a radical of the formula:

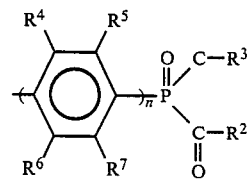

II wherein n is 1 or 2, and $R^4$, $R^5$, $R^6$ and $R^7$ are H, $C_{1-4}$ alkyl, $C_{1-4}$ alkoxyl, F, Cl, or Br;

$R^2$ and $R^3$, which are the same or different, stand for a cyclohexyl, cyclopentyl, phenyl, naphthyl, or biphenylyl radical a cyclopentyl, cyclohexyl, phenyl, naphthyl or biphenylyl radical substituted by F, Cl, Br, I, $C_{1-4}$ alkyl and/or $C_{1-4}$ alkoxyl, or an S or N-containing 5-membered or 6-membered heterocyclic ring; or $R^2$ and $R^3$ are joined to form a ring containing 4 to 10 carbon atoms and being optionally substituted by 1 to 6 $C_{1-4}$ alkyl radicals and at least one polymerizable monomer selected from the group consisting of acrylic acid or methacrylic acid or esters thereof with $C_{1-20}$ monohydric alcohols or polyhydric alcohols; acrylic or methacrylic derivatives of bisphenol A; alkanediol diacrylates or alkanediol dimethacrylates, diacrylates or dimethacrylates of bis-hydroxymethyl tricyclo [5.2.1.0.$^{2,6}$]-decane; reaction products of diisocyanates and hydroxyalkyl(meth)acrylates; adducts of diisocyanates and 2,2-propane-bis-3-(4-phenoxy)-1,2-hydroxypropane-1-methacrylate; adducts of isocyanates and methacroyl alkyl ethers; adducts of isocyanates and methacroyl alkoxybenzoles; adducts of isocyanates and methacroyl alkoxycycloalkanes; aromatic vinyl compounds; styrene or derivatives thereof; α-alkyl derivatives of styrene; unsaturated polyesters prepared by the reaction of α,β-unsaturated dicarboxylic acids in mixture with saturated dicarboxylic acids.

10. A photopolymerizable composition according to claim 9 comprising a bisacylphosphine oxide wherein R is selected from the group consisting of phenyl, 2,5-dimethyl-phenyl, 4-ethoxyphenyl, 4-biphenylyl, 4-propylphenyl, naphthyl, 4-chloro-phenyl, 2,4-dimethoxyphenyl, decyl and 4-octylphenyl and at least one polymerizable monomer selected from the group consisting of methyl methacrylate, ethyl methacrylate, triethylene glycol dimethacrylate, 1,6-hexanediol di(meth)acrylate, 1,4-butandiol di(meth)acrylate, triethylene glycol di(meth)acrylate, tetraethylene glycol di(meth)acrylate, bis-acryloxymethyl-tri-cyclo-[5.2.1.0.$^{2,6}$]-decane, 2,2-bis-4-(3-methacryloxy-2-hydroxypropoxy)-phenylpropane, styrene, α-methylstyrene or vinyl toluene.

* * * * *